US008664265B2

(12) United States Patent
Enose et al.

(10) Patent No.: US 8,664,265 B2
(45) Date of Patent: Mar. 4, 2014

(54) STABLE DOSAGE FORMS OF SPIRO AND DISPIRO 1,2,4-TRIOXOLANE ANTIMALARIALS

(75) Inventors: Arno Appavoo Enose, Kanya Kumari (IN); Harish Kumar Madan, Sonepat (IN); Sumit Madan, New Delhi (IN); Anupam Trehan, New Delhi (IN); Puneet Tyagi, Faridabad (IN); Vinod Kumar Arora, Gurgaon (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 13/183,119

(22) Filed: Jul. 14, 2011

(65) Prior Publication Data

US 2012/0183607 A1    Jul. 19, 2012

Related U.S. Application Data

(63) Continuation-in-part of application No. 11/914,867, filed as application No. PCT/IB2006/051588 on May 18, 2006, now abandoned.

(30) Foreign Application Priority Data

May 18, 2005    (IN) .................................... 1279/2005
May 12, 2006    (IN) .................................... 1192/2006

(51) Int. Cl.
*A61K 31/357*    (2006.01)
*C07D 493/20*    (2006.01)

(52) U.S. Cl.
CPC ............ *A61K 31/357* (2013.01); *C07D 493/20* (2013.01)
USPC ............ 514/462; 514/463; 549/431; 549/433

(58) Field of Classification Search
None
See application file for complete search history.

(56) References Cited

U.S. PATENT DOCUMENTS

| 6,486,199 | B1 | 11/2002 | Vennerstrom et al. | ......... | 514/462 |
| 6,825,230 | B2 * | 11/2004 | Vennerstrom et al. | ......... | 514/462 |
| 2004/0039008 | A1 | 2/2004 | Vennerstrom et al. | ......... | 514/278 |
| 2004/0186168 | A1 | 9/2004 | Vennerstrom et al. | ......... | 514/462 |

OTHER PUBLICATIONS

Meshnick et al., "Artemisinin and the Antimalarial Endoperoxides: from Herbal Remedy to Targeted Chemotherapy", *Microbiological Reviews*, 60(2):301-315 (1996).
Vroman et al., "Current Progress in the Chemistry, Medicinal Chemistry and Drug Design of Artemisinin Based Antimalarials", *Current Pharmaceutical Design*, 5(2):101-138 (1999).
Dhingra et al., "Current status of artemisinin and its derivatives as antimalarial drugs", *Life Sciences*, 66(4):279-300 (2000).
Jefford, 1997. Peroxidic Antimalarials. In: Meyer and Testa, eds. *Advances in Drug Research*. vol. 29. USA: Academic Press Limited, pp. 271-325.
Cumming, Ploypradith, and Posner, 1997. Antimalarial Activity of Artemisinin (Qinghaosu) and Related Trioxanes: Mechanism(s) of Action. In: August, Anders, Murad, and Coyle, eds. *Advances in Pharmacology*. vol. 37, USA: Academic Press, Inc., pp. 253-297.
Dong and Vennerstrom, "Peroxidic antimalarials", *Expert Opinion on Therapeutic Patents*, 11(11):1753-1760 (2001).
Wesche et al., "Neurotoxicity of Artemisinin Analogs In Vitro", *Antimicrobial Agents and Chemotherapy*, 38(8):1813-1819 (1994).
White, "Clinical pharmacokinetics and pharmacodynamics of artemisinin and derivatives", *Transactions of the Royal Society of Tropical Medicine and Hygiene*, 88(Suppl. 1):41-43 (1994).
van Agtmael et al., "Artemisinin drugs in the treatment of malaraia: from medicinal herb to registered medication" *Trends in Pharmacological Sciences*, 20(5):199-205 (1999).
Vennerstrom et al., "Synthesis and Antimalarial Activity of Sixteen Dispiro-1,2,4,5-tetraoxanes: Alkyl-Substituted 7,8,15,16-Tetraoxadispiro[5.2.5.2]hexadecanes", *Journal of Medicinal Chemistry*, 43(14:)2753-2758 (2000).
Hung et al., "Population pharmacokinetics of piperaquine in adults and children with uncomplicated falciparum or vivax malaria", *British Journal of Clinical Pharmacology*, 57(3): 253-262 (2003).
Chapter 45—Oral Solid Dosage Forms. In: Gennaro et al., eds., *Remington: The Science and Practice of Pharmacy*, 20th ed. (2000). USA:Lippincott Williams and Wilkins, pp. 860-861.
Vippagunta et al., "Crystalline solids", *Advanced Drug Delivery Reviews*, 48:3-26 (2001).
Stavchansky and McGinity, 1990. Bioavailability in Tablet Technology. In: Lieberman, Lachman, and Schwartz, eds. *Pharmaceutical Dosage Forms*, vol. 2. USA:Marcel Dekker, Inc., pp. 462-472.
Jain and Mohammedi, "Polymorphism in Pharmacy", *Indian Drugs*, 23(6):315-329 (1986).
Grepioni, "Themed issue: Polymorphism and crystal forms", *New Journal of Chemistry*, 32:1657-1658 (2008).
Braga and Grepioni, "Making crystals from crystals: a green route to crystal engineering and polymorphism", *Chemical Communications*, 2005(29):3635-3645 (2005).
The United States Pharmacopeial Convention and The Council of Experts and its Expert Committees, 2011. Impurities in Drug Substances and Drug Products. In: *United States Pharmacopeia* ("*USP*"), 34th revision, vol. 1, Chapter 1086 (Impurities). Rockville, MD:The United States Pharmacopeial Convention, pp. 607-608.
Dr. B.S. Kakkaliya, 2008. Chemoprophylaxis for Malaria [online]. India, Dr. B.S. Kakkilaya's Malaria Web Site. Available from: http://www.malariasite.com/malaria/Prophylaxis.htm [Accessed Dec. 20, 2010].
Castelli et al., "Malaria Prophylaxis: A Comprehensive Review", *Pharmaceuticals*, 3:3212-3239 (2010).
Uhlemann et al., "Mechanism of Antimalarial Action of the Synthetic Trioxolane RBX11160 (OZ277)", *Antimicrobial Agents and Chemotherapy*, 51(2):667-672 (2007).

\* cited by examiner

*Primary Examiner* — Eric S Olson

(57) ABSTRACT

The field of the invention relates to stable dosage forms comprising spiro or dispiro 1,2,4-trioxolane antimalarials, or their pharmaceutically acceptable salts, prodrugs and analogues, and processes for their preparation. The water content of the dosage form is not more than 6.5% w/w.

21 Claims, No Drawings

STABLE DOSAGE FORMS OF SPIRO AND DISPIRO 1,2,4-TRIOXOLANE ANTIMALARIALS

FIELD OF THE INVENTION

The field of the invention relates to stable dosage forms comprising spiro or dispiro 1,2,4-trioxolane antimalarials, or their pharmaceutically acceptable salts, prodrugs and analogues, and processes for their preparation.

BACKGROUND OF THE INVENTION

Malaria, the most common parasitic disease of humans, remains a major health and economic burden in most tropical countries. Large areas of Central and South America, Hispaniola (Haiti and the Dominican Republic), Africa, the Middle East, the Indian subcontinent, Southeast Asia, and Oceania are considered as malaria-risk areas. It leads to a heavy toll of illness and death especially amongst children and pregnant women. According to the World Health Organization, it is estimated that the disease infects about 400 million people each year, and around two to three million people die from malaria every year. There are four kinds of malaria parasites that infect human: *Plasmodium falciparum, Plasmodium vivax, Plasmodium ovale* and *Plasmodium malariae*.

Malaria spreads from one person to another by the bite of mosquito, Anopheles gambiae which serves as vector. When a mosquito sucks the blood of human, sporozoites are transfused into the human body together with saliva of the mosquito. The sporozoites enter into the hepatocytes, reproduce asexually and finally enter into the blood stream. The parasites continue to multiply inside the red blood cells, until they burst and release large number of merozoites. This process continues, destroying a significant number of blood cells and causing the characteristic paroxysm ("chills and fever") associated with the disease. In the red blood cells, some of the merozoites become male or female gametocytes. These gametocytes are ingested by the mosquito when it feeds on blood. The gametocytes fuse in the vector's gut; sporozoites are produced and are migrated to the vector's salivary glands.

The clinical symptoms of malaria are generally associated with the bursting of red blood cells causing an intense fever associated with chills that can leave the infected individual exhausted and bedridden. More severe symptoms associated with repeat infections and/or infection by *Plasmodium falciparum* include anaemia, severe headaches, convulsions, delirium and, in some instances, death.

Quinine, an antimalarial compound that is extracted from the bark of cinchona tree, is one of the oldest and most effective drugs in existence. Chloroquine and mefloquine are the synthetic analogs of quinine developed in 1940's, which due to their effectiveness, ease of manufacture, and general lack of side effects, became the drugs of choice. The downside to quinine and its derivatives is that they are short-acting and have bitter taste. Further, they fail to prevent disease relapses and are also associated with side effects commonly known as "Chinchonism syndrome" characterized by nausea, vomiting, dizziness, vertigo and deafness. However, in recent years, with the emergence of drug-resistant strains of parasite and insecticide-resistant strains of vector, the treatment and/or control of malaria is becoming difficult with these conventional drugs.

Malarial treatment further progressed with the discovery of Artemisinin (qinghaosu), a naturally occurring endoperoxide sesquiterpene lactone isolated from the plant Artemisia annua (Meshnick, S. R. et al., *Microbiol. Rev.*, 60, 301-315 (1996); Vroman J. A. et al., *Curr. Pharm. Design*, 5, 101-138 (1999); Dhingra V. K. et al., 66, 279-300 (2000)), and a number of its precursors, metabolites and semi synthetic derivatives which have shown to possess antimalarial properties. The antimalarial action of artemisinin is due to its reaction with iron in free heme molecules of the malaria parasite, with the generation of free radicals leading to cellular destruction. This initiated a substantial effort to elucidate its molecular mechanism of action (Jefford, C., dv. *Drug Res.*, 29, 271-325 (1997); Cumming, J. N. et al., *Adv. Pharmacol.*, 37, 254-297 (1997)) and to identify novel antimalarial peroxides (Dong, Y. and Vennerstrom, J. L., *Expert Opin. Ther. Patents*, 11, 1753-1760 (2001)).

Although the clinically useful semi synthetic artemisinin derivatives are rapid acting and potent antimalarial drugs, they have several disadvantages including recrudescence, neurotoxicity, (Wesche, D. L. et al., *Antimicrob. Agents. Chemother.*, 38, 1813-1819 (1994)) and metabolic instability (White, N. J., *Trans. R. Soc. Trop. Med. Hyg.*, 88, 41-43 (1994)). A fair number of these compounds are quite active in vitro, but most suffer from low oral activity (White, N. J., *Trans. R. Soc. Trop. Med. Hyg.*, 88, 41-43 (1994) and van Agtmael et al., *Trends Pharmacol. Sci.*, 20, 199-205 (1999)).

Thus there exists a need in the art to identify new peroxide antimalarial agents, especially those which are easily synthesized, are devoid of neurotoxicity, and which possess improved solubility, stability and pharmacokinetic properties. Following that, many synthetic antimalarial 1,2,4-trioxanes (Jefford, C., *Adv. Drug Res*, 29, 271-325 (1997); Cumming, J. N. et al., *Adv. Pharmacol.*, 37, 254-297 (1997)), 1,2,4,5-tetraoxanes (Vennerstrom, J. L. et al., *J. Med. Chem.*, 43, 2753-2758 (2000)), and other endoperoxides have been prepared. Various patents/applications disclose means and method for treating malaria using Spiro or dispiro 1,2,4-trioxolanes for example, in U.S. Patent Application No. 2004/0186168 and U.S. Pat. Nos. 6,486,199 and 6,825,230. The present invention relates to solid dosage forms of the various Spiro or dispiro 1,2,4-trioxolanes antimalarial compounds disclosed in these patents/applications and are incorporated herein by reference.

Active compounds representing various Spiro and dispiro 1,2,4-trioxolane derivatives possess excellent potency, efficacy against *Plasmodium* parasites, and a lower degree of neurotoxicity, in addition to their structural simplicity and ease of synthesis. Furthermore, these compounds have half lives which are believed to permit short-term treatment regimens comparing favorably to other artemisinin-like drugs. In general, the therapeutic dose of trioxolane derivative may range between about 0.1-1000 mg/kg/day, in particular between about 1-100 mg/kg/day. The foregoing dose may be administered as a single dose or may be divided into multiple doses. For malaria prevention, a typical dosing schedule could be, for example, 2.0-1000 mg/kg weekly beginning 1-2 weeks prior to malaria exposure continued up to 1-2 weeks post-exposure.

However, in spite of many advantages of trioxolanes, there are certain limitations for formulators developing formulations with trioxolones, the first being their susceptibility to degradation in presence of moisture that results in reduced shelf lives. Another is their bitter taste, which can result in poor compliance of the regimen or selection of another, possibly less effective, therapeutic agent.

We have now discovered that a stable antimalarial oral solid dosage form comprising Spiro or dispiro 1,2,4-trioxolanes can be prepared by controlling the water content below a certain critical limit. Further, the bitter taste can be masked by applying a film coating layer to the solid dosage form.

SUMMARY OF THE INVENTION

In one general aspect there is provided a stable oral solid dosage form that includes a therapeutically effective amount of a compound having the structure of Formula I,

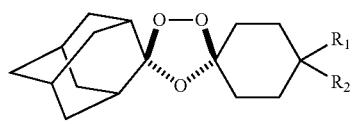

Formula I and its enantiomers, diastereomers, polymorphs, pharmaceutically acceptable salts and pharmaceutically acceptable solvates, wherein:

$R_1$ and $R_2$ are same or different and are selected from hydrogen, substituted or unsubstituted linear or branched alkyl, aryl, and alkaryl groups and substituted or unsubstituted alicyclic groups that are optionally interrupted by one or more oxygen, sulfur or nitrogen atoms, substituted or unsubstituted aromatic or heterocyclic groups that may be interrupted by one or more oxygen, sulfur or nitrogen atoms, a hydroxy group, and a halogen, and further providing that the spirocyclohexyl ring attaching $R_1$ and $R_2$ are optionally interrupted by one or more oxygen, sulfur, or nitrogen atoms; and one or more pharmaceutically acceptable excipients, wherein not more than 5% w/w total related substances are formed on storage at 40°±2° C. and 75%±5% relative humidity over a period of 6 months.

Embodiments of the oral solid dosage form may include one or more of the following features. For example, the dosage form may include one or more of other antimalarial drugs. The other antimalarial drugs may include quinine, mefloquine, lumefantrine, sulfadoxine-pyrimethamine, dihydroartimisinin, piperaquine, chloroquine, amodiaquine, proguanil, atovaquone, chloroproguanil, dapsone, fosmidomycin, tetracycline, DB 289 (pafuramidine maleate), clindamycin, their salts and derivatives thereof. In particular, piperaquine, lumefantrine and DB 289 may be used.

The pharmaceutically acceptable excipients may include one or more of binders, diluents, glidants/lubricants, disintegrants, surfactants and coloring agents.

In another aspect there is provided a stable oral solid dosage form of a therapeutically effective amount of a compound having the structure of Formula I, which is formulated using a dry or non-aqueous process.

The solid dosage form may be in the form of a tablet and the tablet may be coated.

In another general aspect there is provided a process for the preparation of a stable oral solid dosage form. The process includes blending a compound having the structure of Formula I and one or more intragranular excipients; granulating the blend to form granules; blending the granules with one or more extragranular excipients; and compressing the blend into tablet or filling into capsule.

Embodiments of the process may include one or more of the following features. For example, the granulation may be wet granulation and the wet granulation may include a non-aqueous granulating liquid selected from ethanol, isopropyl alcohol, acetone, dichloromethane, and a binder solution. The granulation may be dry granulation and the dry granulation may be compaction or slugging. In particular, the dry granulation may be compaction for example, dry roller compaction.

The tablet may be coated with one or more film coating layers.

In another general aspect there is provided a process for the preparation of a stable oral solid dosage form. The process includes blending a compound having the structure of Formula I, and one or more pharmaceutically acceptable excipients; directly compressing the blend into tablet or filling into capsule; and optionally applying one or more film coating layers to the tablet.

In another general aspect there is provided a process for the preparation of a stable oral solid dosage form. The process includes granulating a blend of one or more excipients; drying the excipient granules; blending excipient granules with a compound having the structure of Formula I, or with granules comprising a compound having the structure of Formula I; compressing the blend into tablet or filling into capsule; and optionally applying one or more film coating layers to the tablet.

Embodiments of the process may include one or more of the following features. For example, the granulation may be wet granulation and the wet granulation may include a granulating liquid selected from water, ethanol, isopropyl alcohol, acetone, dichloromethane, and a binder solution. The granulation may be dry granulation and the dry granulation may be compaction or slugging. In particular, the dry granulation may be compaction for example, dry roller compaction.

In another general aspect there is provided a method of prophylaxis or treatment of malaria. The method includes administering a solid dosage form that includes a therapeutically effective amount of a compound having the structure of Formula I; and one or more pharmaceutically acceptable excipients, wherein not more than 5% w/w total related substances are formed on storage at 40°±2° C. and 75%±5% relative humidity over a period of 6 months.

Embodiments of the oral solid dosage form may include one or more of the following features. For example, the dosage form may include one or more other antimalarial drugs. The other antimalarial drugs may include quinine, mefloquine, lumefantrine, sulfadoxine-pyrimethamine, dihydroartimisinin, piperaquine, chloroquine, amodiaquine, proguanil, atovaquone, chloroproguanil, dapsone, fosmidomycin, tetracycline, DB 289 (pafuramidine maleate), clindamycin, their salts and derivatives thereof. In particular, piperaquine, lumefantrine and DB 289 may be used.

In another aspect there is provided a method of prophylaxis or treatment of malaria. The method includes administering a solid dosage form that includes a therapeutically effective amount of a compound having the structure of Formula I, which is formulated using a dry or non-aqueous process.

In another aspect there is provided a stable oral solid dosage form. The dosage form includes a therapeutically effective amount of a compound having the structure of Formula I; at least one other antimalarial drug selected from lumefantrine, piperaquine, or DB 289; and one or more pharmaceutically acceptable excipients.

Embodiments of the oral dosage form may include one or more of the following features. For example, the water content of the dosage form may not be more than 6.5% w/w.

In another general aspect there is provided a stable oral solid dosage form. The dosage form includes cis-adamantane-2-spiro-3'-8'-[[[(2'-amino-2'-methylpropyl)amino]carbonyl]-methyl]-1',2',4'-trioxaspiro[4.5]decane hydrogen maleate; piperaquine; and one or more pharmaceutically acceptable excipients.

In another general aspect, there is provided a stable oral solid dosage form comprising:
(a) cis-adamantane-2-spiro-3'-8'-[[[(2'-amino-2'-methyl-propyl)amino]carbonyl]-methyl]-1',2',4'-trioxaspiro [4.5]decane hydrogen maleate (Active compound I);
(b) piperaquine; and
(c) one or more pharmaceutically acceptable excipients, wherein the dosage form is prepared by a dry process.

In another general aspect, there is provided a stable oral solid dosage form comprising:
(a) Active compound I and
(b) piperaquine; wherein the total drug content is present in an amount of from about 25% to about 85% w/w based on the total weight of the dosage form.

In another general aspect there is provided a stable oral solid dosage form comprising:
(a) Active compound I in an amount of from about 5% to about 25%; and
(b) piperaquine in an amount of from about 40% to about 80% w/w based on the total weight of the dosage form.

In another general aspect there is provided a stable oral solid dosage comprising:
(a) Active compound I in an amount of from about 5% to about 25%; and
(b) piperaquine in an amount of from about 40% to about 80%; and wherein the total drug content does not exceed 85% w/w based on the total weight of the dosage form.

In another general aspect there is provided a stable oral solid dosage of Active compound I and piperaquine; wherein the dosage form has dissolution performance such that, more than 70% w/w of the Active compound I dissolves within 45 minutes, in a pH 4.5 acetate buffer with 2% Tween 80, in USP type II apparatus.

In another general aspect there is provided a stable oral solid dosage form comprising;
(a) Active compound I; and
(b) piperaquine in a weight ratio of about 1:1 to about 1:10.

In another general aspect there is provided a stable oral solid dosage form comprising Active compound I is present in a dose range of about 100 to about 300 mg and piperaquine is present in a dose range of about 700 to about 850 mg.

In another general aspect there is provided a stable oral solid dosage form comprising;
(a) Active compound I in an amount of from about 5% to about 25%;
(b) piperaquine in an amount of from about 40% to about 80%;
(c) diluent in an amount of from about 10% to about 40%;
(d) disintegrant in an amount of from about 1% to about 10%; and
(e) lubricant in an amount of from about 1% to about 5% w/w based on the total weight of the dosage form.

In another general aspect there is provided a stable oral solid dosage form comprising:
(a) Active compound I;
(b) piperaquine;
(c) microcrystalline cellulose as a diluent;
(d) crospovidone as a disintegrant; and
(e) magnesium stearate as a lubricant.

In another general aspect there is provided a stable oral solid dosage comprising:
(a) Active compound I in an amount of from about 5% to about 25%;
(b) piperaquine in an amount of from about 40% to about 80%; and
(c) microcrystalline cellulose in an amount of from about 10 to about 40% w/w based on the total weight of the dosage form.

In another general aspect there is provided a stable oral solid dosage form comprising the Active compound I and microcrystalline cellulose in a weight ratio of about 1:1 to about 1:5.

The pharmaceutically acceptable excipients may be selected from the group consisting of binders, diluents, glidants/lubricants, disintegrants, surfactants and coloring agents.

The solid dosage form may be in the form of a tablet, capsule, pellets, pills, granules or powder. Particularly the dosage form is a tablet or a capsule. More particularly, the dosage form is a tablet.

In another general aspect there is provided a stable oral solid dosage form, wherein the dosage form is processed and stored at a temperature below 27° C. and relative humidity 50%.

The dry process comprises direct compression or dry granulation.

In another general aspect there is provided a process for the preparation of a stable oral solid dosage form, comprising the steps of:
(a) blending Active compound I, piperaquine, and one or more intragranular excipients;
(b) milling, grinding or sieving the blend by roller compaction to form granules;
(c) blending the granules with one or more extragranular excipients;
(d) compressing the blend into tablets or filling into capsules.

In another general aspect there is provided a process for the preparation of a stable oral solid dosage form, comprising the steps of:
(a) blending Active compound I, piperaquine, and one or more intragranular excipients;
(b) granulating the blend by slugging;
(c) blending the granules with one or more extragranular excipients;
(d) compressing the blend into tablets or filling into capsules.

In another general aspect there is provided a process for the preparation of a stable oral solid dosage form, comprising the steps of:
(a) blending Active compound I, piperaquine, and one or more pharmaceutically acceptable excipients; and
(b) directly compressing the blend into tablets or filling into capsules.

In another general aspect there is provided a process for the preparation of a stable oral solid dosage form, comprising the steps of:
(a) granulating a blend of one or more excipients;
(b) drying the excipient granules;
(c) blending excipient granules with Active compound I and piperaquine; and
(d) compressing the blend into tablets or filling into capsules.

The granulation is particularly dry granulation and the dry granulation may be compaction or slugging. In particular, the dry granulation may be compaction for example, dry roller compaction.

The tablet may be coated with one or more film coating layers.

In another general aspect there is provided a method of treatment of malaria. The method includes administering a stable oral solid dosage form comprising:
(a) Active compound I;
(b) piperaquine; and
(c) one or more pharmaceutically acceptable excipients, wherein the dosage form is prepared by a dry process.

The details of one or more embodiments are set forth in the description below. Other features, objects and advantages of the invention will be apparent from the description and claims.

DETAILED DESCRIPTION OF THE INVENTION

We have now discovered that stable solid oral dosage forms of Spiro or dispiro 1,2,4-trioxolane antimalarials can be prepared which do not degrade significantly and provide acceptable shelf life.

The term "stable" as used herein refers to chemical stability of active compound in solid dosage forms against decomposition occurring during shelf life due to hydrolysis, wherein not more than 5% w/w total related substances are formed on storage at 40°±2° C. and 75%±5% relative humidity over a period of 6 months.

The solid dosage form as used herein is selected from a group consisting of tablets or coated tablets, capsules, pellets, pills, granules, powders, and the like. A particularly suitable solid dosage form is that of tablets.

The present invention provides stable oral solid dosage forms of active compound, by using excipients having low water content and manufactured using dry or non-aqueous formulation processes.

The term "active compound" as used herein includes spiro or dispiro 1,2,4-trioxolane compound of Formula I

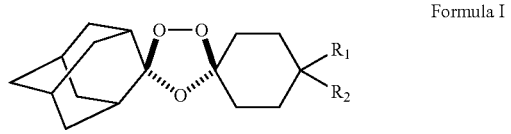

Formula I wherein $R_1$ and $R_2$ are same or different and are selected from hydrogen, substituted or unsubstituted linear or branched alkyl, aryl, and alkaryl groups and substituted or unsubstituted alicyclic groups that are optionally interrupted by one or more oxygen, sulfur or nitrogen atoms, substituted or unsubstituted aromatic or heterocyclic groups that may be interrupted by one or more oxygen, sulfur or nitrogen atoms, a hydroxy group, and a halogen, and further providing that the spirocyclohexyl ring attaching $R_1$ and $R_2$ are optionally interrupted by one or more oxygen, sulfur, or nitrogen atoms. In particular, it includes compounds of Formula I, wherein $R_1$ is hydrogen, for example, compounds having the structure of Formula II.

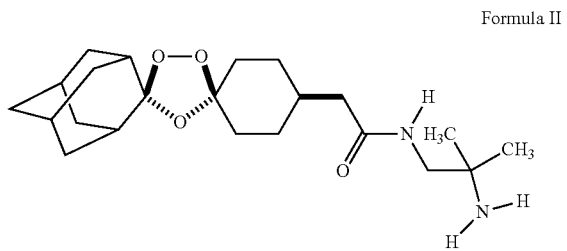

Formula II

Active compound includes one or more of the various spiro and dispiro trioxolane derivatives disclosed in U.S. Application No. 2004/0186168 and U.S. Pat. Nos. 6,486,199 and 6,825,230 and are incorporated herein by reference. These trioxolanes are relatively sterically hindered on at least one side of the trioxolane heterocycle which provides better in vivo activity, especially with respect to oral administration. Particularly, spiro and dispiro 1,2,4-trioxolanes derivatives possess excellent potency and efficacy against Plasmodium parasites, and a lower degree of neurotoxicity.

The term "Active compound I" herein means cis-adamantane-2-spiro-3'-8'-[[[(2'-amino-2'-methylpropyl)amino]carbonyl]-methyl]-1',2',4'-trioxaspiro[4.5]decane hydrogen maleate. The Active compound I may be present in an amount of from about 5% to about 25%, w/w based on the total dosage form.

Further, perceiving the potential threat of malarial parasite developing resistance towards otherwise very potent, artemisinin class of drugs, WHO has called for an immediate halt to provision of single-drug artemisinin malaria pills. In the case of malaria, combination therapy has been applied since around 1990. However, this strategy is being hampered because the Plasmodium parasite has developed resistance, as a result of monotherapy, to certain components of currently applied combination drugs. Combination therapy is expected to retard the development of resistance, improve efficacy by lowering recrudescence rate, provide synergistic effect, and increase exposure of the parasite to the drugs.

Embodiments of the oral solid dosage of the present invention further include one or more of antimalarial drugs. The antimalarial drugs may include quinine, mefloquine, lumefantrine, sulfadoxine-pyrimethamine, dihydroartimisinin, piperaquine, chloroquine, amodiaquine, proguanil, atovaquone, chloroproguanil, dapsone, fosmidomycin, tetracycline, DB 289 (pafuramidine maleate), clindamycin, their salts and derivatives thereof In particular, piperaquine, lumefantrine and DB 289 may be used; however piperaquine remains the preferred one.

Selection of combination as an antimalarial therapy is based on certain attributes. Synthetic artemisinin derivatives exhibit their action by their reaction with the iron in free heme molecules in the malaria parasite with the generation of free radicals leading to cellular destruction. On the other hand bisquinoline derivatives such as piperaquine interfere with the detoxification of haemin in the digestive vacuole of the parasite to non-toxic malaria pigment, so that haemin can generate free radicals and membrane damage follows. The unrelated mode of action of the two drugs would provide improved therapy, and treatment against all stages of parasites including gametocytes. Additionally since, synthetic artemisinin derivatives are very efficacious and highly potent; these would thereby treat the symptoms quickly, exhibiting fast recovery rates. Combination of synthetic artemisinin derivatives and bisquinoline derivatives such as piperaquine provide a short duration of treatment.

Piperaquine is a bisquinoline compound that has antimalarial activity against both P. vivax and P. falciparum, including strains of chloroquine resistant P. falciparum. The tolerability, efficacy, pharmacokinetic profile, low cost and longer-acting piperaquine makes it a very perfect candidate for use in combination with short and rapidly acting Active compound I. Piperaquine of the present invention includes piperaquine phosphate. Piperaquine may be present in an amount of from about 40% to about 80% w/w based on the total dosage form.

The total drug content of the oral dosage forms of the present invention may vary from about 25% to about 85%, in particular may not exceed 85% w/w based on the total dosage form.

The oral dosage forms of the present invention comprise Active compound I and piperaquine in a weight ratio of about 1:1 to about 1:10.

The oral dosage forms of the present invention comprise Active compound I present in a dose range of about 100 mg to about 300 mg and piperaquine present in a dose range of about 700 mg to about 850 mg.

It has been observed through exhaustive experimentation that when active compound is formulated into dosage forms, including liquid as well as solid dosage forms, it gets degraded by hydrolysis. The degradation may be due to water associated with the excipients or added during the course of processing. Thus, liquid oral dosages forms such as aqueous syrups, suspensions or solutions having desired shelf life could not be successfully prepared. Further, preparation of solid oral dosage forms of active compound, using techniques involving use of water such as wet granulation, spray drying, or extrusion-spheronization processes, resulted in dosage forms with wavering stability results. However, acceptable stability results were obtained when the solid dosage forms were formulated using appropriate excipients with low water content and a process in which water was absent, such as dry granulation, direct compression or non-aqueous granulation. In case where excipients were granulated using water, the excipient granules were dried appropriately before blending with active compound as such or with active compound containing granules, and processed into solid dosage forms of acceptable stability.

The role of excipients and water content was evaluated by conducting compatibility studies of active compound with various excipients, in different proportions and evaluating the extent of degradation by forced degradation at 60° C. over the period of 2 weeks and at 50° C. for 4 weeks. The water content was analyzed using Karl Fischer method and the total related substances (% w/w) were determined by HPLC method. The results of the study are represented below in Table 1.

TABLE 1

Compatibility studies of active compound (Active compound I) with various excipients

| Excipient | Drug: Excipient | Water (% w/w) | Initial | Total Related Substance (% w/w) After 4 weeks/ 50° C. | After 2 weeks/ 60° C. |
|---|---|---|---|---|---|
| Croscarmellose sodium | 1:0.5 | 0.59 | 0.09 | 0.34 | 0.35 |
| Cross povidone | 1:0.5 | 3.49 | 0.13 | 0.40 | 0.68 |
| Sodium starch glycolate | 1:0.5 | 1.43 | 0.13 | 0.43 | 0.89 |
| Hydroxypropyl methylcellulose 5 cps | 1:0.5 | 1.22 | 0.17 | 0.70 | 1.05 |
| Polyvinyl pyrrolidone K 30 | 1:0.5 | 3.02 | 0.00 | 0.33 | 0.79 |
| Sodium lauryl sodium | 1:0.5 | 0.79 | 0.15 | 0.92 | 1.59 |
| Opadry ® | 1:0.5 | 0.46 | 0.17 | 1.85 | 0.96 |
| Titanium dioxide | 1:0.5 | 0.18 | 0.16 | 0.57 | 0.93 |
| Talc | 1:0.1 | 0.12 | 0.15 | 0.63 | 0.90 |
| Mg. Stearate | 1:0.1 | 0.46 | 0.13 | 0.65 | 0.86 |
| Aerosol | 1:0.1 | 0.27 | 0.14 | 0.66 | 0.86 |
| Polyethylene glycol 400 | 1:0.1 | 0.88 | 0.14 | 0.66 | 0.68 |
| Microcrystalline cellulose | 1:2 | 3.69 | 0.19 | 0.70 | 0.74 |
| Starch | 1:2 | 4.73 | 0.08 | 0.60 | 0.74 |
| Dicalcium phosphate | 1:2 | 2.01 | 0.07 | 0.77 | 1.32 |
| Pearlitol | 1:2 | 0.02 | 0.14 | 0.72 | 0.77 |
| Micro crystalline cellulose | 1:10 | 4.94 | 0.39 | 0.78 | 1.02 |
| Starch | 1:10 | — | 0.07 | 0.60 | 4.13 |
| Dicalcium phosphate | 1:10 | 2.14 | 0.17 | 0.61 | 6.07 |
| Pearlitol | 1:10 | 0.52 | 0.14 | 0.46 | 0.70 |

The study clearly indicates the importance of use of excipients having low water or moisture content in stabilizing solid dosage forms of active compound. In the present invention, we have discovered that the use of excipients having water content less than 6.5% w/w surprisingly increases the stability of the active compound, and thus provides reasonably long shelf lives. Starch was found to be incompatible with active compound when used in higher amounts. Further, lactose was also found to be incompatible due to degradation by other mechanisms such as Maillard reaction, and dicalcium phosphate was not preferred due to increase in related substances at 60° C. Microcrystalline cellulose, however, gave the most satisfactory results.

The stable oral solid dosage forms of the present invention may further comprise one or more pharmaceutically acceptable excipients, which include all physiologically inert excipients used in the art for the preparation of solid dosage forms. Examples include binders, diluents, glidants/lubricants, disintegrants, surfactants, coloring agents, and the like. The excipients may be used either intragranularly or extragranularly, or both. The weight ratio of active compound and excipients in the dosage forms may vary from about 1.5:1 to about 1:30.

Examples of "binders" include methyl cellulose, hydroxypropyl cellulose, hydroxypropyl methylcellulose, polyvinylpyrrolidone, gelatin, gum arabic, ethyl cellulose, polyvinyl alcohol, pullulan, agar, tragacanth, sodium alginate, and the like.

Examples of "diluents" include cellulose powdered, microcrystalline cellulose, dextrates, dextrins, dextrose excipients, fructose, kaolin, lactitol, mannitol, sorbitol, sucrose, sugar compressible, sugar confectioners, in particular microcrystalline cellulose. The diluents may be present in an amount from about 10% to about 40% w/w based on the total weight of the dosage form. Further, the weight ratio of Active compound I to microcrystalline cellulose may vary from about 1:1 to about 1:5.

Examples of "disintegrants" include clays, celluloses, alginates, gums, cross-linked polymers (such as cross-linked polyvinylpyrrolidone and cross-linked sodium carboxymethylcellulose), sodium starch glycolate, low-substituted hydroxypropyl cellulose and soy polysaccharides, in particular crospovidone. The disintegrant may be present in an amount from about 1% to about 10% w/w based on the total weight of the dosage form.

Examples of "lubricants" or "glidants" include talc, magnesium stearate, calcium stearate, stearic acid, colloidal silicon dioxide, magnesium carbonate, magnesium oxide, calcium silicate, microcrystalline cellulose, mineral oil, waxes, glyceryl behenate, polyethylene glycol, sodium benzoate, sodium acetate, sodium chloride, sodium laurylsulfate, sodium stearyl fumarate, hydrogenated vegetable oils, sucrose esters of fatty acid, microcrystalline wax, yellow beeswax, white beeswax, and the like, in particular magnesium stearate. The lubricant may be present in an amount from about 1% to about 5% w/w based on the total weight of the dosage form.

Examples of "surfactants" include both non-ionic and ionic (cationic, anionic and zwitterionic) surfactants suitable for use in sweetener compositions. These include polyethoxylated fatty acids and its derivatives, for example polyethylene glycol 400 distearate, polyethylene glycol-20 dioleate, polyethylene glycol 4-150 mono dilaurate, polyethylene glycol-20 glyceryl stearate; alcohol-oil transesterification products, for example polyethylene glycol-6 corn oil; polyglycerized fatty acids, for example polyglyceryl-6 pentaoleate; propylene glycol fatty acid esters, for example propylene glycol monocaprylate; mono and diglycerides, for example glyceryl ricinoleate; sterol and sterol derivatives; sorbitan fatty acid esters and its derivatives, for example polyethylene glycol-20 sorbitan monooleate, sorbitan monolaurate; polyethylene glycol alkyl ether or phenols, for example polyethylene glycol-20 cetyl ether, polyethylene glycol-10-100 nonyl phenol; sugar esters, for example sucrose monopalmitate; polyoxyethylene-polyoxypropylene block copolymers known as "poloxamer"; ionic surfactants, for example sodium caproate, sodium glycocholate, soy lecithin, sodium stearyl fumarate, propylene glycol alginate, octyl sulfosuccinate disodium, and palmitoyl carnitine.

The "coloring agents" include any FDA approved colors for oral use.

The solid dosage forms may further be coated with one or more functional and/or non-functional layers comprising film-forming polymers, and other coating additives.

Examples of "film-forming polymers" include cellulose derivatives such as ethyl cellulose, hydroxypropyl methylcellulose, hydroxypropylcellulose, methylcellulose, carboxymethylcellulose, hydroxymethylcellulose, hydroxyethylcellulose, partially hydrolyzed polyvinyl alcohol, cellulose acetate, hydroxypropyl methylcellulose phthalate, cellulose acetate phthalate, cellulose acetate trimellitate; waxes such as polyethylene glycol; methacrylic acid polymers such as Eudragit® RL and RS; and the like. Alternatively, commercially available coating compositions comprising film-forming polymers marketed under various trade names, such as Opadry® may also be used for coating.

The "coating additives" comprise one or more of plasticizers, glidants or flow regulators, opacifiers and lubricants.

The pharmaceutical acceptable excipients and/or film forming polymers and coating additives may be selected to provide immediate release profile or modified release profile.

Solid dosage forms of Active compound I may be prepared by densifying Active compound I and one or more excipients, and processing into solid dosage forms. Densification may be carried out using any conventional method known in the art. In particular, granulation or extrusion-spheronization may be used.

In one of the embodiments, a stable oral tablet of Active compound I may be prepared by a process comprising the steps of blending Active compound I and intragranular portion of a diluent, lubricant, and disintegrant; passing the blend through a roller compactor to form a compact mass; reducing the compact into granules of suitable size; blending the granules with extragranular portion of a lubricant, disintegrant, and diluent in a double cone blender; and finally compressing into tablets using suitable tooling.

In another embodiment, a stable oral tablet of Active compound I may be prepared by a process comprising the steps of blending Active compound I, intragranular portion of a diluent, lubricant, and disintegrant; compressing the blend in a heavy tabletting press to form slugs; reducing the slugs into granules of suitable size; blending the granules with extragranular portion of a lubricant, disintegrant, and diluent in a double cone blender; and finally compressing into tablets using suitable tooling.

In another embodiment, a stable oral capsule of Active compound I may be prepared by a process comprising the steps of blending Active compound I, intragranular portion of a diluent, lubricant, and disintegrant; passing the blend through a roller compactor to form a compact mass; reducing the compact mass into granules of a suitable size; blending the granules with extragranular portion of a lubricant in a double cone blender; and finally filling into capsules of a suitable size.

In another embodiment, a stable oral capsule of Active compound I may be prepared by a process comprising the steps of blending Active compound I, intragranular portion of a diluent, lubricant, and disintegrant; compressing the blend in a heavy tabletting press to form slugs; reducing the slugs into granules of a suitable size; blending the granules with extragranular portion of lubricant in a double cone blender; and finally filling into capsules of a suitable size.

In another embodiment, a stable oral tablet of Active compound I may be prepared by a process comprising the steps of blending Active compound I, a diluent, a lubricant and a disintegrant; and directly compressing into tablets using suitable tooling.

In another embodiment, a stable oral capsule of Active compound I may be prepared by a process comprising the steps of blending Active compound I, a diluent, and a lubricant; and filling into capsules of a suitable size.

In another embodiment, a stable oral tablet of Active compound I may be prepared by a process comprising the steps of blending Active compound I, intragranular portion of a diluent, and disintegrant; wet granulating the blend with a non aqueous granulating fluid or a solution/dispersion of pharmaceutically acceptable excipients in the non-aqueous granulating fluid; drying and reducing the granules to a suitable size; blending the granules with extragranular portion of a lubricant, disintegrant and diluent in a double cone blender; and finally compressing into tablets using suitable tooling.

In yet another embodiment, a stable oral capsule of Active compound I may be prepared by a process comprising the steps of blending Active compound I, intragranular portion of diluent, and disintegrant; wet granulating the blend with a non aqueous granulating fluid or a solution/dispersion of pharmaceutically acceptable excipients in the non-aqueous granulating fluid; drying and reducing the granules to a suitable size; blending the granules with extragranular portion of lubricant in a double cone blender; and finally filling into capsules of a suitable size.

Examples of "non-aqueous granulating fluid" include organic solvents such as methanol, ethanol, isopropyl alcohol, dichloromethane, acetone, and the like.

In yet another embodiment, tablets prepared by any of the above described processes may further be coated with film forming polymers and one or more coating additives, using techniques well known in the art such as spray coating in a conventional coating pan or a fluidized bed processor; or dip coating. Alternatively, coating can also be performed using a hot melt technique.

The coating layers over the tablet may be applied as a solution/dispersion of coating components in a suitable solvent. Examples of solvents used for preparing a solution/dispersion of the coating ingredients include methyl alcohol, ethyl alcohol, isopropyl alcohol, n-butyl alcohol, acetone, acetonitrile, chloroform, methylene chloride, water and the like, and mixtures thereof.

In still another embodiment, one or more of another antimalarial drug selected from piperaquine, lumefantrine, and DB 289 (pafuramidine maleate) may be added in the blend comprising active compound, in any of the embodiments above.

The dosage form of the present invention is processed and stored at a temperature below 27° C. and relative humidity 50%.

The invention described herein is further illustrated by the following examples, which should not be construed as limitation the scope of the invention.

EXAMPLE 1

| Ingredients | % w/w |
|---|---|
| Intragranular | |
| Maleate salt of a compound of Formula II (active compound) [Active compound I] | 43.2 |
| Microcrystalline Cellulose | 46.67 |
| Magnesium stearate | 0.75 |
| Extragranular | |
| Microcrystalline Cellulose | 5.63 |
| Croscarmellose sodium | 3.0 |
| Magnesium stearate | 0.75 |
| Coating | |
| Opadry ® OY SS 58910 white | 2.5 |
| Water | q.s |
| Total weight | 615 |
| Water content | <6.55% w/w |

Procedure:

1. Active compound and intragranular portion of microcrystalline cellulose were sieved through sieve BSS #44 and mixed together in a double cone blender to form a uniform blend.
2. To the blend of step 1, intragranular portion of sifted magnesium stearate was added and blended for about 5 minutes.
3. The blend of step 2 was compacted in a roller compactor and was sifted through sieve BSS #22 to form granules.
4. Extragranular portion of microcrystalline cellulose, croscarmellose sodium and magnesium stearate were sieved through sieve BSS #44 and blended with the granules of step 3.
5. The blend of step 4 was compressed using suitable size punches to obtain compressed tablets.
6. The tablets as obtained from step 5 were coated with Opadry® using conventional coating techniques.

The tablets prepared as per Example 1 were subjected to stability studies at 25° C./RH 60%, 30° C./RH 65% and 40° C./RH 75% over a period of 6 months. The results are summarized in Table 2. The results of in vitro drug release analyzed at predetermined time periods are given in Table 3.

TABLE 2

| | Total related substances (% w/w)* | | | | |
|---|---|---|---|---|---|
| Storage Condition | Initial | 1 months | 2 months | 3 months | 6 months |
| 25° C. and 60% relative humidity | 0.11 | — | — | 0.27 | 0.28 |
| 30° C. and 65% relative humidity | 0.11 | 0.37 | 0.27 | 0.29 | 0.34 |
| 40° C. and 75% relative humidity | 0.11 | 0.55 | 0.67 | 1.40 | 1.82 |

*% Total Related Substance should not be more than 5%

TABLE 3

Percentage (%) of In vitro drug release in USP II apparatus (media: 2% tween 80 in water, 900 ml 75, rpm, in 45 min)*

| Storage Condition | Initial | 1 months | 2 months | 3 months | 6 months |
|---|---|---|---|---|---|
| 25° C. and 60% relative humidity | 93 | — | — | 101 | 95 |
| 30° C. and 65% relative humidity | 93 | 98 | 93 | 94 | 96 |
| Temperature 40° C. and 75% relative humidity | 93 | 98 | 96 | 92 | 94 |

*The in vitro drug release (% w/w) should not be less than 70% (Q) of the labeled amount dissolved in 45 minutes.

As evident from the above studies, the tablets prepared by the process of the present invention in which water is absent show acceptable shelf stability.

EXAMPLE 2

| | Ingredients | % w/w |
|---|---|---|
| 1 | Maleate salt of a compound of Formula II (active compound) [Active compound I] | 44.33 |
| 2 | Microcrystalline Cellulose | 51.17 |
| 3 | Magnesium stearate | 1.5 |
| 4 | Croscarmellose sodium | 3.0 |
| | Total weight | 600 mg |
| | Water content | <6.5% |

Procedure:

1. Active compound, microcrystalline cellulose, croscarmellose sodium and magnesium stearate were sifted through sieve BSS #44.
2. Sifted active compound, microcrystalline cellulose, and croscarmellose sodium were mixed in a double cone blender for about 15 minutes to form a uniform blend.
3. To the blend of step 2, sifted magnesium stearate was added and mixed for about 5 minutes.
4. The blend obtained in step 3 was directly compressed using suitable size capsule shape punches to obtain compressed tablets.

EXAMPLES 3 AND 4

| Ingredients | Example 3 % w/w | Example 4 % w/w |
|---|---|---|
| Intragranular | | |
| Maleate salt of a compound of Formula II (active compound) [Active compound I] | 7.68 | 13.8 |

| Ingredients | Example 3 % w/w | Example 4 % w/w |
|---|---|---|
| Piperaquine phosphate | 61.80 | 55.5 |
| Microcrystalline Cellulose | 20.39 | 21.05 |
| Magnesium stearate | 0.44 | 0.39 |
| Crospovidone | 2.21 | 1.99 |
| Extragranular | | |
| Microcrystalline Cellulose | 4.42 | 3.99 |
| Crospovidone | 2.21 | 1.99 |
| Magnesium stearate | 1.05 | 1.09 |
| Coating | | |
| Opadry ® O2B53782 orange | 2.5 | 2.5 |
| Water | q.s | q.s |
| Total weight (mg) | 1332.5 | 738 |
| Water content | <6.55% w/w | <6.55% w/w |

Procedure:
1. Active compound, piperaquine phosphate and intragranular portion of microcrystalline cellulose and crospovidone were sieved through sieve BSS #44 and mixed together in a double cone blender to form a uniform blend.
2. To the blend of step 1, intragranular portion of sifted magnesium stearate was added and blended for about 5 minutes.
3. The blend of step 2 was compacted in a roller compactor and was sifted through sieve BSS #18 to form granules.
4. Extragranular portion of microcrystalline cellulose and crospovidone were sieved through sieve BSS #44 and blended with the granules of step 3.
5. Extragranular portion of magnesium stearate were sieved through sieve BSS #44 and blended with the blend of step 4, in a double cone blender for about 5 minutes.
6. The blend of step 5 was compressed using suitable size punches to obtain compressed tablets.
7. The tablets as obtained from step 6 were coated with Opadry® using conventional coating techniques and weight built of up to 2.5% w/w.

The tablets prepared as per the Example 3 and 4 were subjected to stability studies at 40° C./RH 75% over a period of 3 months, as represented in Table 4.

TABLE 4

Percentage total related substances (% w/w)*

| Ingredient | | Initial | 1 month | 2 months | 3 months |
|---|---|---|---|---|---|
| Maleate salt of a compound of Formula II [Active compound I] | Example 3 | 0.19 | 0.27 | 0.44 | 0.54 |
| | Example 4 | 0.25 | 0.32 | 0.45 | 0.54 |
| Piperaquine phosphate | Example 3 | 1.16 | 1.1 | 1.11 | 1.16 |
| | Example 4 | 1.15 | 1.03 | 1.13 | 1.16 |

*% Total related substance should not be more than 5%

EXAMPLE 5

| Ingredients | % w/w |
|---|---|
| Intragranular | |
| Active compound I | 14.6 |
| Piperaquine phosphate | 56.3 |
| Microcrystalline Cellulose | 16.7 |
| Magnesium stearate | 0.43 |
| Crospovidone | 2.15 |
| Extragranular | |
| Microcrystalline Cellulose | 4.29 |
| Crospovidone | 2.15 |
| Magnesium stearate | 0.97 |
| Coating | |
| Opadry ® O2B53782 orange | 2.40 |
| Water | q.s |
| Total weight (mg) | 1332.0 |
| Water content | <6.55% w/w |

Procedure:
1. Active compound I, piperaquine phosphate and intragranular portion of microcrystalline cellulose and crospovidone were sieved through sieve BSS #44 and mixed together.
2. To the blend of step 1, intragranular portion of sifted magnesium stearate was added and blended for about 5 minutes.
3. The blend of step 2 was compacted and compacts were sifted through sieve BSS #18 to form granules.
4. Extragranular portion of microcrystalline cellulose and crospovidone were sieved through sieve BSS #44 and blended with the granules of step 3.
5. Extragranular portion of magnesium stearate was sieved through sieve BSS #44 and blended with the blend of step 4, in a double cone blender for about 5 minutes.
6. The blend of step 5 was compressed using suitable size punches to obtain compressed tablets.
7. The tablets as obtained from step 6 were coated with Opadry® using conventional coating techniques and weight built of up to 2.4% w/w.

TABLE 5

Percentage (% w/w) of In vitro drug release of Active compound I, from example 5, in USP II apparatus (media: 2% tween 80 in water, 900 ml, 75 rpm)*

| Time (minutes) | (% w/w) |
|---|---|
| 15 | 88 |
| 30 | 87 |
| 45 | 90 |

*The in vitro drug release (% w/w) should not be less than 70% (Q) of the labeled amount dissolved in 45 minutes.

While several particular formulations have been described, it will be apparent that various modifications and combinations of the formulations detailed in the text can be made without departing from the spirit and scope of the invention. For example, although the tablet dosage form has been prepared, other conventional solid dosage forms like capsule can also be prepared using the similar compositions. Accordingly, it is not intended that the inventions be limited, except as by the appended claims.

We claim:
1. A stable oral solid dosage form comprising; (a) cis-adamantane-2-spiro-3'-8'-[[[(2'-amino-2'-methylpropyl)amino]carbonyl]-methyl]-1',2',4'-trioxaspiro[4.5]decane hydrogen maleate (Active compound I); (b) piperaquine; and (c) one or more pharmaceutically acceptable excipients; wherein the dosage form is prepared by a dry process.
2. The stable oral solid dosage form according to claim 1, wherein the dosage form comprises; (a) Active compound I in an amount of from about 5% to about 25%; and (b) piperaquine in an amount from about 40% to about 80% w/w based on the total weight of the dosage form.

3. The stable oral solid dosage form according to claim 1, wherein the pharmaceutically acceptable excipient is selected from the group consisting of binders, diluents, glidants/lubricants, disintegrants, surfactants and coloring agents.

4. The stable oral solid dosage form according to claim 3, wherein the diluent is microcrystalline cellulose.

5. The stable oral solid dosage form according to claim 1, wherein the dosage form has dissolution performance such that more than 70% w/w of the Active compound I dissolves within 45 minutes, in a pH 4.5 acetate buffer with 2% tween 80, in USP type II apparatus.

6. The stable oral solid dosage form according to claim 1, wherein the Active compound I and piperaquine are present in a weight ratio of from about 1:1 to about 1:10.

7. The stable oral solid dosage form according to claim 1, wherein the Active compound I is present in a dose range of about 100 mg to about 300 mg and piperaquine is present in a dose range of about 700 mg to about 850 mg.

8. The stable oral solid dosage form according to claim 1, wherein the dosage form comprises: (a) Active compound I in an amount of from about 5% to about 25%; (b) piperaquine in an amount of from about 40% to about 80%; (c) diluent in an amount of from about 10% to about 40%; (d) disintegrant in an amount of from about 1% to about 10%; and (e) lubricant in an amount of from about 1% to about 5% w/w based on the total weight of the dosage form.

9. The stable oral solid dosage form according to claim 1, wherein the dosage form comprises: (a) Active compound I; (b) piperaquine; (c) microcrystalline cellulose as a diluent; (d) crospovidone as a disintegrant; and (e) magnesium stearate as a lubricant.

10. The stable oral solid dosage form according to claim 1, wherein the dosage form comprises: (a) Active compound I in an amount of from about 5% to about 25%; (b) piperaquine in an amount of from about 40% to about 80%, and (c) microcrystalline cellulose in an amount of from about 10% to about 40% w/w based on the total weight of the dosage form.

11. The stable oral solid dosage form according to claim 1, wherein the dosage form comprises Active compound I and microcrystalline cellulose in a weight ratio of from about 1:1 to about 1:5.

12. The stable oral solid dosage form according to claim 1, wherein the dosage form is selected from a group consisting of tablet, capsule, pill, granule and powder.

13. The stable oral solid dosage form according to claim 12, wherein the tablet is coated with one or more functional and or non-functional coating layers comprising film-forming polymers and coating additives.

14. The stable oral solid dosage form according to claim 13, wherein the coating additives comprise one or more of plasticizers, glidants or flow regulators, opacifiers and lubricants.

15. The stable oral solid dosage form according to claim 1, wherein the dosage form is processed and stored at a temperature below 27° C. and relative humidity 50%.

16. The stable oral solid dosage form according to claim 1, wherein the dry process comprises direct compression or dry granulation.

17. The stable oral solid dosage form according to claim 1, wherein the dosage form is prepared by a process comprising the steps of: (a) blending Active compound I, piperaquine, and one or more intragranular excipients; (b) milling, grinding or sieving the blend by roller compaction to form granules; (c) blending the granules with one or more extragranular excipients; (d) compressing the blend into tablets or filling into capsules.

18. The stable oral solid dosage form according to claim 1, wherein the dosage form is prepared by a process comprising the steps of: (a) blending Active compound I, piperaquine, and one or more intragranular excipients; (b) granulating the blend by slugging; (c) blending the granules with one or more extragranular excipients; (d) compressing the blend into tablets or filling into capsules.

19. The stable oral solid dosage form according to claim 1, wherein the dosage form is prepared is prepared by a process comprising the steps of: (a) blending Active compound I, piperaquine, and one or more pharmaceutically acceptable excipients; and (b) directly compressing the blend into tablets or filling into capsules.

20. The stable oral solid dosage form according to claim 1, wherein the dosage form is prepared by a process comprising the steps of: (a) granulating a blend of one or more excipients; (b) drying the excipient granules; (c) blending excipient granules with Active compound I and piperaquine; and (d) compressing the blend into tablets or filling into capsules.

21. A method of treatment of malaria, the method comprising administering a stable oral solid dosage form comprising: (a) Active compound I; (b) piperaquine; and (c) one or more pharmaceutically acceptable excipients, wherein the dosage form is prepared by a dry process.

* * * * *

UNITED STATES PATENT AND TRADEMARK OFFICE
CERTIFICATE OF CORRECTION

PATENT NO. : 8,664,265 B2  
APPLICATION NO. : 13/183119  
DATED : March 4, 2014  
INVENTOR(S) : Arno Appavoo Enose et al.

Page 1 of 1

It is certified that error appears in the above-identified patent and that said Letters Patent is hereby corrected as shown below:

ON THE TITLE PAGE:

"(30) Foreign Application Priority Data  
May 18, 2005 (IN)................1279/2005  
May 12, 2006 (IN)................1192/2006"

should read

-- (30) Foreign Application Priority Data  
May 18, 2005 (IN)................1279/DEL/2005  
May 12, 2006 (IN)................1192/DEL/2006 --

IN THE SPECIFICATION:

COLUMN 2, LINE 40:

"Spiro and dispiro 1,2,4-trioxolanes" should read -- spiro and dispiro 1,2,4-trioxolanes --

COLUMN 8, LINE 38:

"salts and derivatives thereof In particular, piperaquine" should read -- salts and derivatives thereof. In particular, piperaquine --

Signed and Sealed this  
Third Day of February, 2015

Michelle K. Lee  
*Deputy Director of the United States Patent and Trademark Office*